US006153751A

United States Patent [19]
Liotta et al.

[11] Patent Number: 6,153,751
[45] Date of Patent: *Nov. 28, 2000

[54] METHOD AND COMPOSITIONS FOR THE SYNTHESIS OF BCH-189 AND RELATED COMPOUNDS

[75] Inventors: Dennis C. Liotta, McDonough, Ga.; Woo-Baeg Choi, North Brunswick, N.J.

[73] Assignee: Emory University, Atlanta, Ga.

[*] Notice: This patent is subject to a terminal disclaimer.

[21] Appl. No.: 09/337,910

[22] Filed: Jun. 22, 1999

Related U.S. Application Data

[63] Continuation of application No. 08/472,345, Jun. 7, 1995, Pat. No. 5,914,400, which is a continuation of application No. 08/215,498, Mar. 21, 1994, abandoned, which is a continuation of application No. 08/015,992, Feb. 10, 1993, Pat. No. 5,539,116, which is a division of application No. 07/473,318, Feb. 1, 1990, Pat. No. 5,204,466.

[51] Int. Cl.⁷ .............................................. C07D 411/04
[52] U.S. Cl. ........................................................... 544/319
[58] Field of Search ............................................. 544/319

[56] References Cited

U.S. PATENT DOCUMENTS

| 4,000,137 | 12/1976 | Dvonoch et al. | 260/252 |
|---|---|---|---|
| 4,336,381 | 6/1982 | Nagata et al. | 544/313 |

(List continued on next page.)

FOREIGN PATENT DOCUMENTS

| 0 337 713 | 4/1989 | European Pat. Off. |
|---|---|---|
| 0 375 329 | 6/1990 | European Pat. Off. |
| 0 382 526 | 8/1990 | European Pat. Off. |
| 0 433 898 | 6/1991 | European Pat. Off. |
| 0 494 119 | 7/1992 | European Pat. Off. |
| 0 515 144 | 11/1992 | European Pat. Off. |
| 0 515 156 | 11/1992 | European Pat. Off. |
| 0 515 157 | 11/1992 | European Pat. Off. |
| 0 526 253 | 2/1993 | European Pat. Off. |
| WO91/17159 | 11/1991 | WIPO . |
| WO92/15308 | 9/1992 | WIPO . |
| WO96/18517 | 10/1992 | WIPO . |

OTHER PUBLICATIONS

Ulrich Niedballa and Helmut Vorbruggen in "Nucleic Acid Chemistry", Leroy B. Townsend Ed., 1979, John–Wiley & Sons, New York, p 431–433.
Kotick et al, JOC, 34, 1969, 3806–3813.
Choi, W.B., et al., J. Am. Chem. Soc., 1991, 113, p. 9377–9379.
Pearson, R.G., J. Am. Chem. Soc., 1963, 85, p. 3533–3539.
Lowry, T.H., et al., Mechanism and Theory in Organic Chemistry, 2nd Ed., Harper & Row, Publishers, NY, pp. 281–287 (1968).
Annunziata, R., et al., *Tetrahedron Letters*, 1990, 6733.
Balzarini, J., et al., *Biochemical and Biophysical Research Communications*, vol. 140, No. 2, pp. 735–742 (1986).
Barlett, P. A.,*J. Am. Chem. Soc.* 1983, 105:2088.
Belleau, B., et al., "Design and Activity of a Novel Class of Nucleoside Analogs Effective Against HIV–1," *5th International Conference on AIDS,* Montreal, Quebec, Canada, Jun. 4–9, 1989.

(List continued on next page.)

*Primary Examiner*—John M. Ford
*Assistant Examiner*—Thomas McKenzie
*Attorney, Agent, or Firm*—Sherry M. Knowles, Esq.; King & Spalding

[57] ABSTRACT

The present invention relates to a method of preparing BCH-189 and various analogs of BCH-189 from inexpensive precursors with the option of introducing functionality as needed. This synthetic route allows the stereoselective preparation of the biologically active isomer of these compounds, β-BCH-189 and related compounds. Furthermore, the steochemistry at the nucleoside 4' position can be controlled to produce enantiomerically-enriched β-BCH-189 and its analogs.

1 Claim, 4 Drawing Sheets

U.S. PATENT DOCUMENTS

| | | | |
|---|---|---|---|
| 4,861,759 | 8/1989 | Mitsuya et al. | 514/46 |
| 4,879,277 | 11/1989 | Mitsuya et al. | 514/49 |
| 4,916,122 | 4/1990 | Chu et al. | 514/50 |
| 4,963,533 | 10/1990 | de Clerq et al. | 514/49 |
| 5,011,774 | 4/1991 | Farina et al. | 435/87 |
| 5,041,449 | 8/1991 | Belleau et al. | 544/317 |
| 5,047,407 | 9/1991 | Belleau et al. | 514/254 |
| 5,059,690 | 10/1991 | Zahler et al. | 544/317 |
| 5,204,466 | 4/1993 | Liotta et al. | 544/317 |
| 5,538,975 | 7/1996 | Dionne . | |
| 5,539,116 | 7/1996 | Liotta et al. | 544/317 |
| 5,618,820 | 4/1997 | Dionne . | |
| 5,639,787 | 6/1997 | Mansour . | |
| 5,663,320 | 9/1997 | Mansour . | |
| 5,684,164 | 11/1997 | Belleau et al. | 549/30 |
| 5,696,254 | 12/1997 | Mansour . | |
| 5,700,937 | 12/1997 | Liotta . | |
| 5,728,575 | 3/1998 | Liotta . | |
| 5,744,596 | 4/1998 | Mansour . | |
| 5,756,706 | 5/1998 | Mansour . | |
| 5,814,639 | 6/1998 | Liotta . | |
| 5,827,727 | 10/1998 | Liotta . | |
| 5,892,025 | 6/1999 | Liotta . | |
| 5,914,331 | 6/1999 | Liotta . | |
| 5,914,400 | 6/1999 | Liotta et al. | 544/314 |

OTHER PUBLICATIONS

Carter, et al., "Activities of (−)–Carbovir and 3'–Azido–3'–Deoxythymidine Against Human Immunodeficiency Virus in Vitro," *Antimicrobial Agents and Chemotherapy,* vol. 34, No. 6, pp. 1297–1300 (1990).

Chang, Chien–Neng, et al., "Deoxycytidine Deaminase–resistant Stereoisomer Is the Active Form of (±)–2', 3'–Didedoxy–3'–thiacytidine in the Inhibition of Hepatitis B Virus Replication," *The Journal of Biological Chemistry,* vol. 357, No. 20, pp. 13938–13942 (1992).

Choi et al., *J. Am. Chem. Soc.,* vol. 113, No. 24, 1991. *Chem. Ber.,* 114:1244 (1981).

Chu, C. K., *Nucleosides & Nucleotides,* 1989, 8:903.

Chu, et al., "Comparative Activity of 2',3'–Saturated and Unsaturated Pyrimidine and Purine Nucleosides Against Human Immunodeficiency Virus Type 1 in Peripheral Blood Mononuclear Cells," *Biochem. Pharm.,* vol. 37, No. 19, pp. 3543–3548 (1988).

Chu, C. K., et al., "En Efficient Total Synthesis of 3'–Azido–3'–Deoxythiamidine (AZT) and 3'–Azido–2', 3'–Dideoxyuridine (AZDDU, CS–87) from D–Mannitol," *Tetrahedron Letters,* 1988, p. 5349.

Cretton, E., et al., "Pharmakinetics of 3'–Azido–3'–Deoxythymidine and its Catabolites and Interactions with Probenecid in Rhesus Monkeys," *Antimicrobial Agents and Chemotherapy,* pp. 801–807 (1991).

Evans, D. A. et al. *J. Am. Chem. Soc.,* 1990, 112:8215.

Furman, et al., "The Anti–Hepatitis B Virus Activities, Cytotoxicities, and Anabolic Profiles of the (−) and (+) Enantiomers of cis–5–Fluoro–1–[2–(Hydromethyl)–1, 3–Oxathiolan–5–yl] Cytosine," *Antimicrobial Agents and Chemotherapy,* vol. 36, No. 12, pp. 2686–2692 (1992).

Hoong, et al., *Journal of Organic Chemistry,* 1992, vol. 57, pp. 5563–5565.

Jeong, L., et al., "Asymmetric Synthesis and Biological Evaluation of β–L–(2R,5S)– and α–L–(2E,5R)–1,3–Oxathiolane –Pyrimidine and –Purine Nucleosides and Potential Anti–HIV Agents," *J. Med. Chem.,* vol. 36 (1993).

Lin, et al., "Potent and Selective In Vitro Activity of 3'–Deoxythyminidin–2–ene–(3'–Deoxy–2',3'–Didehydrothymidine) Against Human Immunodeficiency Virus," *Biochem. Pharm.,* vol. 36, No. 17, p. 2716 (1987).

Mitsuya, H., et al., "Rapid in Vitro Systems for Assessing Activity of Agents Against HTLV–III/LAV," *AIDS: Modern Concepts and Therapeutic Challenges,* S. Broder, Ed. (Marcel–Dekker, New York), (1987), p. 303.

Mitsuya, H. et al., *Proc. Natl. Acad. Sci. USA,* vol. 82, pp. 7097–7100 (1985).

Mitsuya, H. et al., "Molecular Targets for AIDS Therapy," *Science,* vol. 249, pp. 1533–1544 (1990).

Nicolaou, K. C., *J. Am. Chem. Soc.,* 1986, 108:2466.

Norbeck, D., et al., "A New 2',3'–Dideoxynucleoside Prototype with an In Vitro Activity Against HIV," *Tetrahedron Lett.* (1989), p. 6263.

Okabe, M. et al., "Synthesis of the Dideoxynucleosides ddC and CNT from Glutamic Acid, Ribonolactone, and Pyrimidine Bases," *J. Org. Chem.,* 1989, 53:4780.

Richman, D. et al., "The Toxicity of Azidothymidine (AZT) in the Treatment of Patients with AIDS and AIDS–Related Complex," *N. Eng. J. Med.,* (1987) 317:192.

Satsumabayashi, S. et al., "The Synthesis of 1,3–Oxathiolan–5–one Derivatives," *Bull. Chem. Soc. Japan,* 1972, 45, 913.

Schinazi, R. F. et al., *Antimicrobial Agents and Chemotherapy* 36(3) p. 672–676 (1992).

Schinazi, R. F. et al., "Insights into HIV Chemotherapy," *AIDS Research and Human Retroviruses* 8(6) (1992) p. 963–990.

Schinazi, R. F. et al., *Antimicrobial Agents and Chemotherapy,* 36(11) pp. 2432–2438 (1992).

Schinazi, R. F., et al., "Substrate Specificity of *Escherichia Coli* Thymidine Phosphorylase for Pyrimidine Nucleoside with an Anti–Human Immunodeficiency Virus Activity," *Biochemical Pharmacology* 44(2) (1992) 199–204.

Storer, Richard, et al., *Nucleosides & Nucleotides,* 12(2), 225–236 (1993).

Takano, A., et al., *Chemistry Letters,* 1983, p. 1593.

Vorbruggen et al., "Nucleoside Synthesis with Trimethylsilyl Triflate and Perchlorate as Catalysts," *Chem. Ber.* 1981, 114:1234–1255.

Wilson, L. J., et al., "A General Method for Controlling Glycosylation Stereochemistry in the Synthesis of 2'–Deoxyribose Nucleosides," *Tetrahedron Lett.* 1990, p. 1815.

Winslow, Dean L. et al., *AIDS,* vol. 8, No. 6, pp. 753–755 (1994).

Zhu, Zhou, et al., *Molecular Pharmacology,* vol. 38, pp. 929–938 (1990).

METHOD AND COMPOSITIONS FOR THE SYNTHESIS OF BCH-189 AND RELATED COMPOUNDS

This application is a continuation U.S. Ser. No. 08/472, 345, filed on Jun. 7, 1995, now U.S. Pat. No. 5,914,400, which is a continuation of U.S. Ser. No. 08/215,498 filed Mar. 21, 1994, now abandoned which is a continuation of U.S. Ser. No. 08/015,992 filed Feb. 10, 1993 now U.S. Pat. No. 5,539,116, which is a divisional of U.S. Ser. No. 07/473,318 filed Feb. 1, 1990, issued Apr. 20, 1993 as U.S. Pat. No. 5,204,466, the contents of which are incorporated by reference.

TECHNICAL FIELD

The present invention relates to methods and compositions for preparing antiviral nucleoside analogs, particularly BCH-189 (2',3'-dideoxy-3'-thia-cytidine). More particularly, the invention relates to the selective synthesis of the β-isomer of BCH-189 and related compounds as well as the selective synthesis of enantiomerically-enriched BCH-189 and related compounds.

BACKGROUND ART

In 1981, documentation began on the disease that became known as Acquired Immune Deficiency Syndrome (AIDS), as well as its forerunner AIDS Related Complex (ARC). In 1983, the cause of the disease AIDS was established as a virus named the Human Immunodeficiency Virus type 1 (HIV-1). Usually, a person infected with the virus will eventually develop AIDS; in all known cases of AIDS the final outcome has always been death.

The disease AIDS is the end result of an HIV-1 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single stranded DNA. The viral RNA is degraded and a second DNA strand is created. The now double-stranded DNA is integrated into the human cell's genes and those genes are used for cell reproduction.

At this point, the human cell carries out its reproductive process by using its own RNA polymerase to transcribe the integrated DNA into viral RNA. The viral RNA is translated into glycoproteins, structural proteins, and viral enzymes, which assemble with the viral RNA intact. When the host cell finishes the reproductive step, a new virion cell, not a T-4 lymphocyte, buds forth. The number of HIV-1 virus cells thus grows while the number of T-4 lymphocytes decline.

The typical human immune system response, killing the invading virion, is taxed because a large portion of the virion's life cycle is spent in a latent state within the immune cell. In addition, viral reverse transcriptase, the enzyme used in making a new virion cell, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to grow while the immune response system continues to weaken. Eventually, the HIV largely holds free reign over the body's immune system, allowing opportunistic infections to set in and ensuring that, without the administration of antiviral agents and/or immunomodulators, death will result.

There are three critical points in the virus' life cycle which have been identified as targets for antiviral drugs: (1) the initial attachment of the virion to the T-4 lymphocyte, or macrophage, site, (2) the transcription of viral RNA to viral DNA, and (3) the assemblage of the new virion cell during reproduction.

Inhibition of the virus at the second critical point, the viral RNA to viral DNA transcription process, has provided the bulk of the therapies used in treating AIDS. This transcription must occur for the virion to reproduce because the virion's genes are encoded in RNA; the host cell reads only DNA. By introducing drugs that block the reverse transcriptase from completing the formation of viral DNA, HIV-1 replication can be stopped.

Nucleoside analogs, such as 3'-azido-3'-deoxythymidine (AZT), 2',3'-dideoxycytidine (DDC), 2',3'-dideoxythymidinene (D4T), 2',3'-dideoxyinosine (DDI), and various fluoro-derivatives of these nucleosides are relatively effective in halting HIV replication at the reverse transcriptase stage. Another promising reverse transcriptase inhibitor is 2',3'-dideoxy-3'-thia-cytidine (BCH-189), which contains an oxathiolane ring substituting for the sugar moiety in the nucleoside.

AZT is a successful anti-HIV drug because it sabotages the formation of viral DNA inside the host T-4 lymphocyte cell. When AZT enters the cell, cellular kinases activate AZT by phosphorylation to AZT triphosphate. AZT triphosphate then competes with natural thymidine nucleosides for the receptor site of HIV reverse transcriptase enzyme. The natural nucleoside possesses two reactive ends, the first for attachment to the previous nucleoside and the second for linking to the next nucleoside. The AZT molecule has only the first reactive end; once inside the HIV enzyme site, the AZT azide group terminates viral DNA formation because the azide cannot make the 3',5'-phosphodiester with the ribose moiety of the following nucleoside.

AZT's clinical benefits include increased longevity, reduced frequency and severity of opportunistic infections, and increased peripheral CD4 lymphocyte count. Immunosorbent assays for viral p24, an antigen used to track HIV-1 activity, show a significant decrease with use of AZT. However, AZT's benefits must be weighed against the severe adverse reactions of bone marrow suppression, nausea, myalgia, insomnia, severe headaches, anemia, peripheral neuropathy, and seizures. Furthermore, these adverse side effects occur immediately after treatment begins whereas a minimum of six weeks of therapy is necessary to realize AZT's benefits.

Both DDC and D4T are potent inhibitors of HIV replication with activities comparable (D4T) or superior (DDC) to AZT. However, both DDC and D4T are converted to their 5' triphosphates less efficiently than their natural analogs and are resistant to deaminases and phosphorylases. Clinically, both compounds are toxic. Currently, DDI is used to conjunction with AZT to treat AIDS. However, DDI's side effects include sporadic pancreatis and peripheral neuropathy. Initial tests on 3'-fluoro-2'-3'-dideoxythymidine show that its anti-viral activity is comparable to that of AZT.

Recent tests on BCH-189 have shown that it possesses anti-HIV activity similar to AZT and DDC, but without the cell toxicity which causes the debilitating side effects of AZT and DDC. A sufficient quantity of BCH-189 is needed to allow clinical testing and treatment using the drug.

The commonly-used chemical approaches for synthesizing nucleosides or nucleoside analogs can be classified into two broad categories: (1) those which modify intact nucleosides by altering the carbohydrate, the base, or both and (2) those which modify carbohydrates and incorporate the base, or its synthetic precursor, at a suitable stage in the synthesis. Because BCH-189 substitutes a sulfur atom for a carbon atom in the carbohydrate ring, the second approach is more feasible. The most important factor in this latter strategy involves delivering the base from the β-face of the carbohydrate ring in the glycosylation reaction because only the β-isomers exhibit useful biological activity.

It is well known in the art that the stereoselective introduction of bases to the anomeric centers of carbohydrates can be controlled by capitalizing on the neighboring group participation of a 2-substituent on the carbohydrate ring (*Chem. Ber.* 114:1234 (1981)). However, BCH-189 and its analogs do not possess a 2-substitutent and, therefore, cannot utilize this procedure unless additional steps to introduce a functional group that is both directing and disposable are incorporated into the synthesis. These added steps would lower the overall efficiency of the synthesis.

It is also well known in the art that "considerable amounts of the undesired α-nucleosides are always formed during the synthesis of 2'-deoxyribosides" (*Chem. Ber.* 114:1234, 1244 (1981)). Furthermore, this reference teaches that the use of simple Friedel-Crafts catalysts like $SnCl_4$ in nucleoside syntheses produces undesirable emulsions upon the workup of the reaction mixture, generates complex mixtures of the α and β-isomers, and leads to stable δ-complexes between the $SnCl_4$ and the more basic silyated heterocycles such as silyated cytosine. These complexes lead to longer reaction times, lower yields, and production of the undesired unnatural N-3-nucleosides. Thus, the prior art teaches the use of trimethysilyl triflate or trimethylsilyl perchlorate as a catalyst during the coupling of pyrimidine bases with a carbohydrate ring to achieve high yields of the biologically active β-isomers. However, the use of these catalysts to synthesize BCH-189 or BCH-189 analogs does not produce the β-isomer preferentially; these reactions result in approximately a 50:50 ratio of the isomers.

Thus, there exists a need for an efficient synthetic route to BCH-189 and its analogs. There also exists a need for a stereoselective synthetic route to the biologically active isomer of these compounds, β-BCH-189 and related β-analogs. Furthermore, there exists a need for a stereoselective synthetic route to enantiomerically-enriched β-BCH-189 because the other enantiomer is inactive and, therefore, represents a 50% impurity.

DISCLOSURE OF INVENTION

The present invention relates to the discovery of a surprisingly efficient synthetic route to BCH-189 and various analogs of BCH-189 from inexpensive precursors with the option of introducing functionality as needed. This synthetic route allows the stereoselective preparation of the biologically active isomer of these compounds, β-BCH-189 and related compounds. Furthermore, the steochemistry at the nucleoside 4' position can be controlled to produce enantiomerically-enriched β-BCH-189 and its analogs.

The term "BCH-189 analogs" is meant to refer to nucleosides that are formed from pyrimidine bases substituted at the 5 position that are coupled to substituted 1,3-oxathiolanes.

The method of the present invention includes ozonizing an allyl ether or ester having the formula $CH_2$=CH—$CH_2OR$, in which R is a protecting group, such as an alkyl, silyl, or acyl group, to form a glycoaldehyde having the formula OHC—$CH_2$—OR; adding thioglycolic acid to the glycoaldehyde to form a lactone of the formula 2-(R-oxy)-methyl-5-oxo-1,3-oxathiolane; converting the lactone to its corresponding carboxylate at the 5 position of the oxathiolane ring; coupling the acetate with a silyated pyrimidine base in the presence of $SnCl_4$ to form the β-isomer of a 5'-(R-oxy)-2',3'-thia-nucleoside analog; and replacing the R protecting group with a hydrogen to form BCH-189 or an analog of BCH-189.

The invention can be used to produce BCH-189 or BCH-189 analogs that are enantiomerically-enriched at the 4' position by selecting an appropriate R protecting group to allow stereoselective selection by an enzyme. For instance, the R protecting group can be chosen such that the substituent at the 2 position of the oxathiolane lactone is butyryloxy to permit stereoselective enzymatic hydrolysis by pig liver esterase. The resulting optically active hydrolyzed lactone can then be converted to its corresponding diacetate and coupled with a silyated pyrimidine base as above.

Accordingly, one of the objectives of this invention is to provide an efficient method for preparing the β-isomer of BCH-189 and analogs of BCH-189 in high yields. Furthermore, it is an objective of this invention to provide a synthetic method to produce only one optical isomer, rather than a racemic mixture, of BCH-189 and analogs of BCH-189. A further object of this invention is to provide a synthetic route to produce β-BCH-189 that is enantiomerically-enriched.

Additionally, an objective of this invention is to provide intermediates from which BCH-189 or BCH-189 analogs can be synthesized of the formula 2-(R-oxymethyl)-5-acyloxy-1,3-oxathiolane, wherein R is a protecting group, such as alkyl, silyl, or acyl, and a method of preparing these compounds. Furthermore, it is an object of this invention to provide enantiomerically-enriched 2-acetoxymethyl-5-acetoxy-1,3-oxathiolane and 2-butoxymethyl-5-oxo-1,3-oxathiolane and methods of preparing these compounds.

Another objective of this invention is to provide intermediates from which BCH-189 or BCH-189 analogs can be synthesized of the formula:

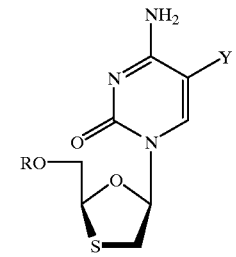

wherein R is a protecting group, such as alkyl, silyl, or acyl, and Y can be hydrogen, methyl, halo, alkyl, alkenyl, alkynl, hydroxalkyl, carboxalkyl, thioalkyl, selenoalkyl, phenyl, cycloalkyl, cycloalkenyl, thioaryl, and selenoaryl, and methods of preparing these compounds.

Furthermore, this invention provides intermediates from which BCH-189 or BCH-189 analogs can be synthesized of the formula:

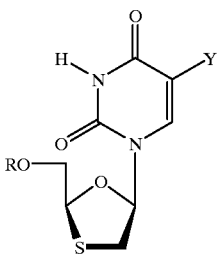

wherein R is a protecting group, such as alkyl, silyl, or acyl, and Y can be hydrogen, methyl, halo, alkyl, alkenyl, alkynyl, hydroxalkyl, carboxalkyl, thioalkyl, selenoalkyl, phenyl, cycloalkyl, cycloalkenyl, thioaryl, and selenoaryl, and methods of preparing these compounds.

BEST MODE OF CARRYING OUT THE INVENTION

BCH-189 is a compound of the formula:

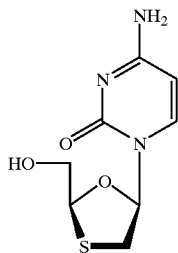

Figure 1:
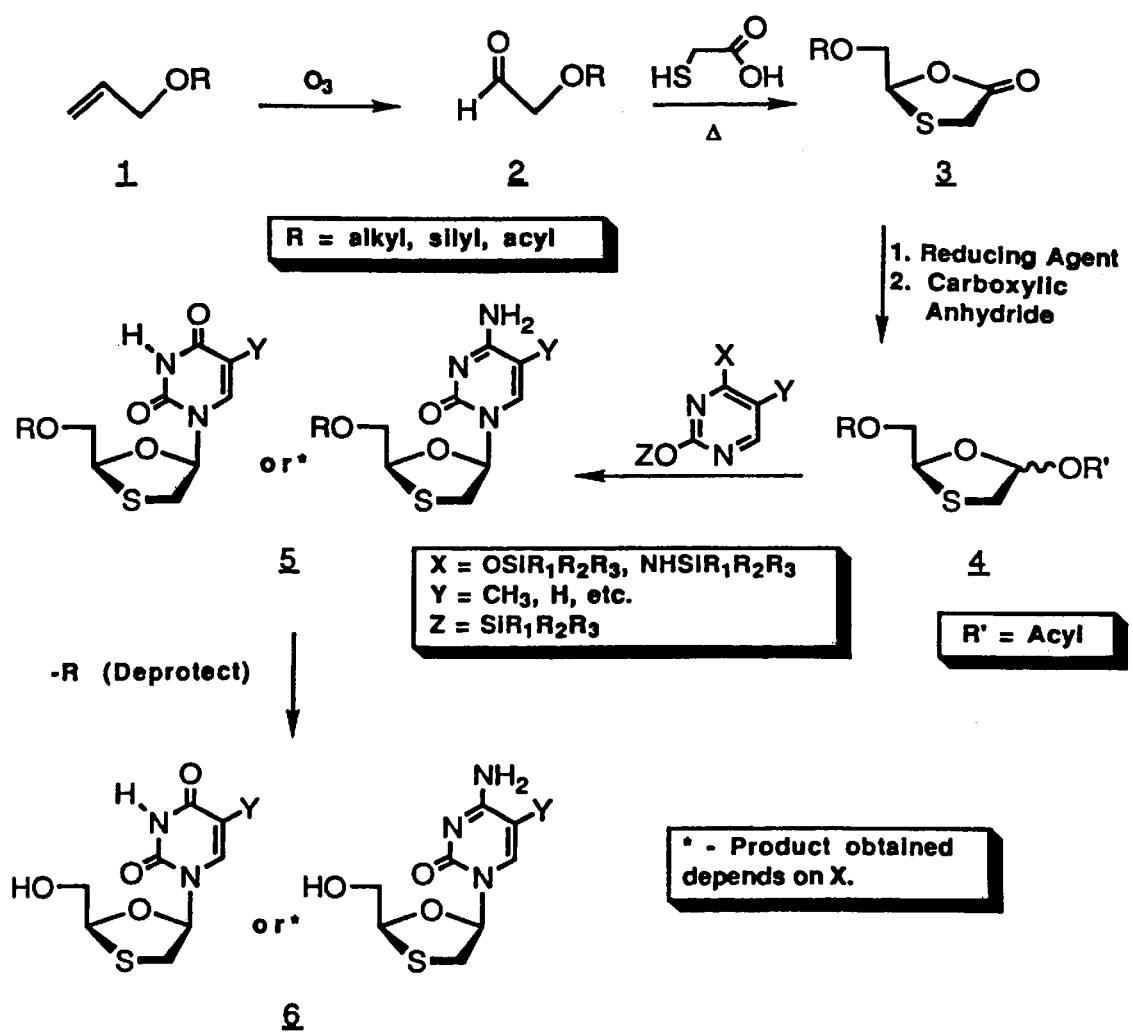
FIG. 1 illustrates one embodiment of a synthesis of BCH-189 and BCH-189 analogs according to the present invention.

The process of the present invention for preparing BCH-189 and BCH-189 analogs is set forth in FIG. 1. An allyl ether or ester 1 is ozonized to give an aldehyde 2, which reacts with thioglycolic acid to give a lactone 3. The lactone 3 is treated with a reducing agent, followed by a carboxylic anhydride, to produce the carboxylate 4. This carboxylate is coupled with a silyated pyrimidine base in the presence of a Lewis acid that can catalyze stereospecific coupling, such as $SnCl_4$, to yield the β-isomer of the substituted nucleoside 5 in essentially a 100:0 ratio of β:α isomers. The substituted nucleoside 5 is deprotected to produce BCH-189 or BCH-189 analog 6.

This procedure can be tailored to produce BCH-189 or BCH-189 analogs that are enantiomerically-enriched at the 4' position by selecting an appropriate R protecting group to allow stereoselective enzymatic hydrolysis of 3 by an enzyme such as pig liver esterase, porcine pancreatic lipase, or subtilisin or other enzymes that hydrolyze 3 in a stereoselective fashion. The resulting optically active 3 can be converted to enantiomerically-enriched carboxylate 4 and coupled with a silyated pyrimidine base as above to produce enantiomerically-enriched BCH-189 or BCH-189 analogs.

The protecting group R in 1 can be selected to provide protection for the corresponding alcohol until the final step in the synthesis is carried out (deprotection of 5 to form 6). Additionally, the protecting group can be selected, if desired, to provide an additional recognition site for an enzyme to be used later in an enantio-selective hydrolysis reaction. Any group that functions in this matter may be used. For instance, alkyl, silyl, and acyl protecting groups or groups that possess substantially the same properties as these groups can be used.

An alkyl protecting group, as used herein, means triphenylmethyl or an alkyl group that possesses substantially the same protecting properties as triphenylmethyl. A silyl protecting group, as used herein, means a trialkylsilyl group having the formula:

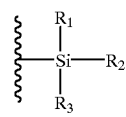

wherein $R_1$, $R_2$, and $R_3$ may be lower-alkyl, e.g., methyl, ethyl, butyl, and alkyl possessing 5 carbon atoms or less; or phenyl. furthermore, $R_1$ may be identical to $R_2$; $R_1$, $R_2$, and $R_3$ may all be identical. Examples of silyl protecting groups include, but are not limited to, trimethylsilyl and t-butyldiphenylsilyl.

An acyl group, as used herein to describe an acyl protecting group (as in 1) or to describe a carboxylate (as in 4), is a group having the formula:

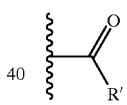

wherein R' is a lower alkyl, e.g., methyl, ethyl, butyl, and alkyl possessing 5 carbon atoms or less; substituted lower alkyl wherein the alkyl bears one, two, or more simple substituents, including, but not limited to, amino, carboxyl, hydroxy, phenyl, lower-alkoxy, e.g., methoxy and ethoxy; phenyl' substituted phenyl wherein the phenyl bears one, two, or more simple substituents, including, but not limited to, lower alkyl, halo, e.g., chloro and bromo, sulfato, sulfonyloxy, carboxyl, carbo-lower-alkoxy, e.g., carbomethoxy and carbethoxy, amino, mono- and di-lower alkylamino, e.g., methylamino, amido, hydroxy, lower alkoxy, e.g., methoxy and ethoxy, lower-alkanoyloxy, e.g., acetoxy.

A silyated pyrimidine base, as used herein, means a compound having the formula:

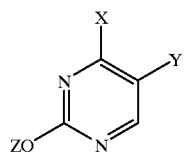

wherein X is either a trialkylsilyloxy or a trialkylsilylamino group, Z is a trialkylsilyl group, and Y is further described below. A trialkylsilyl group, as used herein, means a group having the formula:

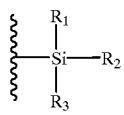

wherein $R_1$, $R_2$, and $R_3$ may be lower-alkyl, e.g., methyl, ethyl, butyl, and alkyl possessing 5 carbon atoms or less, or phenyl. Furthermore, $R_1$ may be identical to $R_2$; $R_1$; $R_2$, and $R_3$ may all be identical. Examples of trialkylsilyl groups include, but are not limited to, trimethylsilyl and t-butyldiphenylsilyl.

The silyated pyrimidine base may be substituted with various Y substituents, including, but not limited to, hydrogen, methyl, halo, alkyl, alkenyl, alkynyl, hydroxyalkyl, carboxyalkyl, thioalkyl, selenoalkyl, phenyl, cycloalkyl, cycloalkenyl, thioaryl, and selenoaryl, at position 5 of the silyated pyrimidine base (Y substituent in FIG. 1) to modify the properties, such as transport properties or the rate of metabolism, of the BCH-189 analog.

Figure 2:
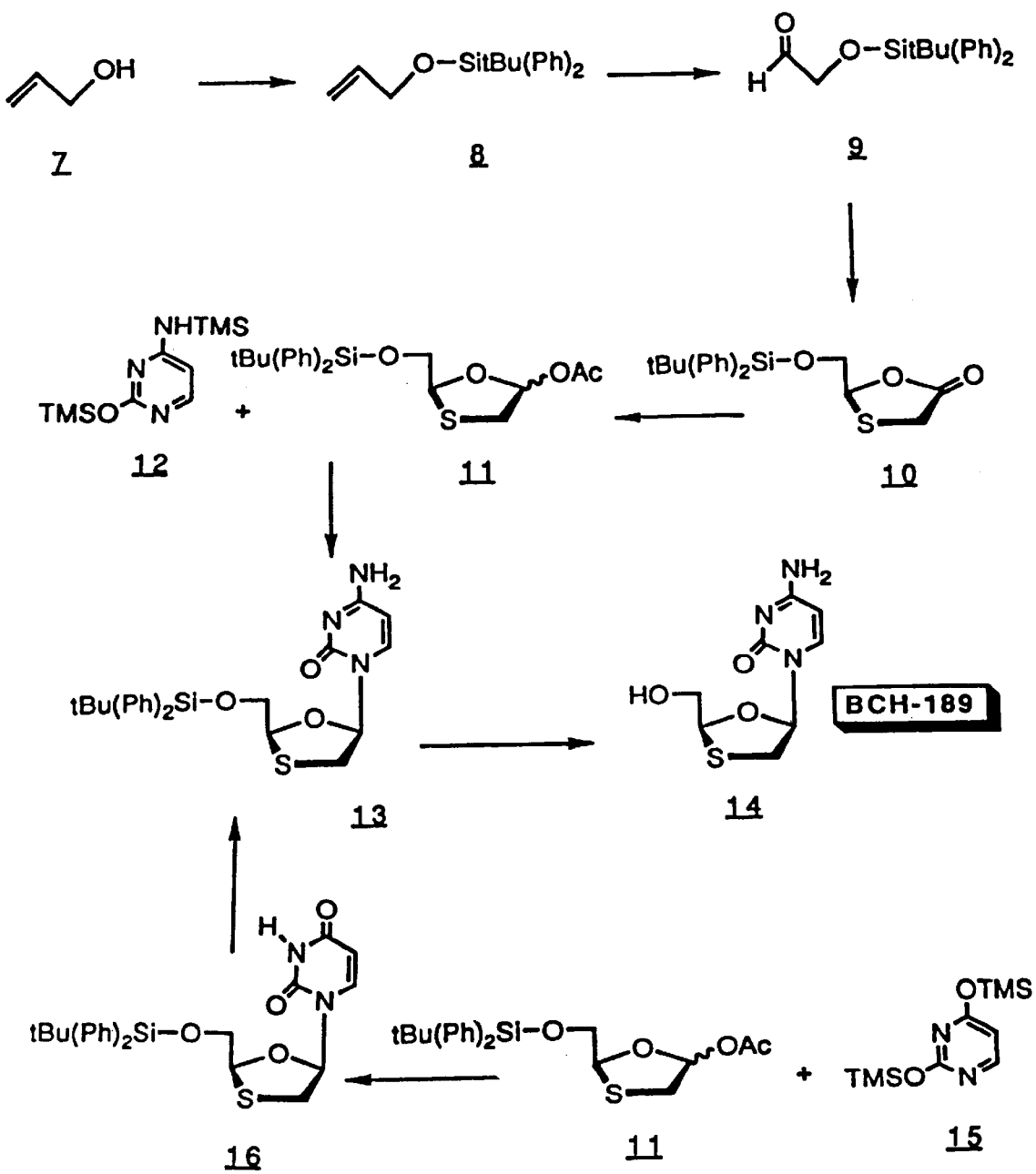
FIG. 2 illustrates one embodiment of the synthesis of BCH-189 according to the present invention.
Figure 3:
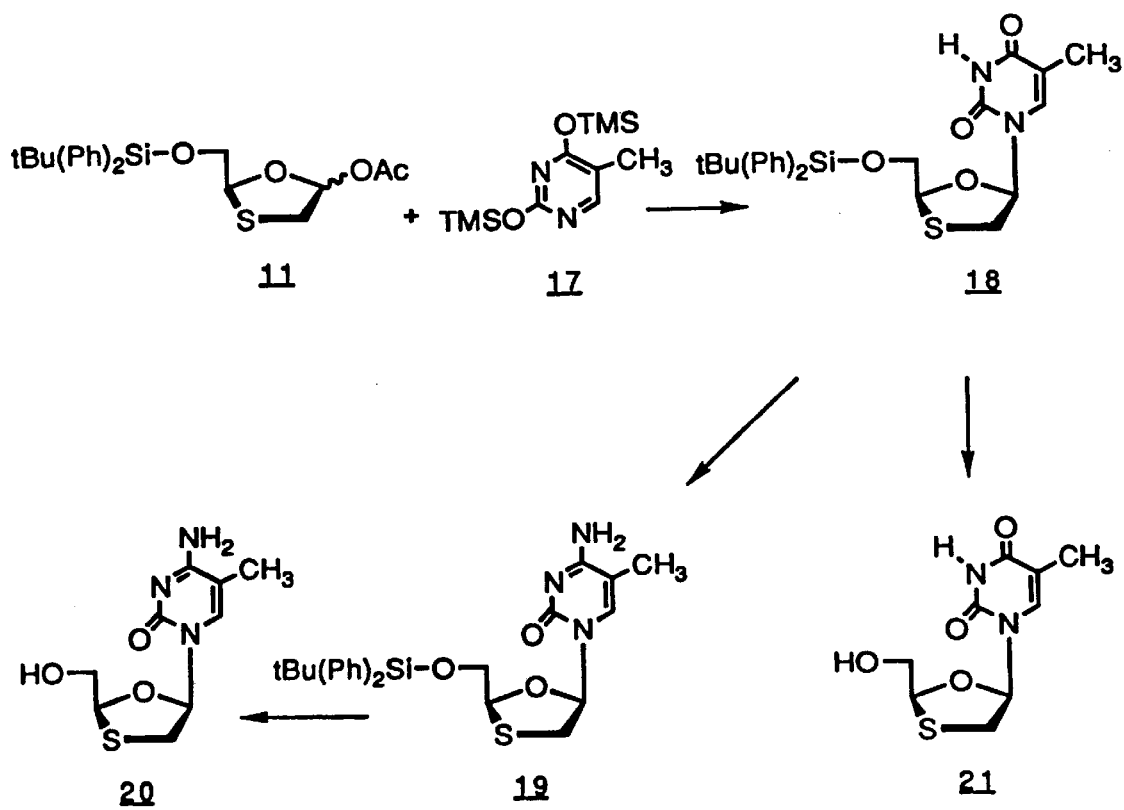
FIG. 3 illustrates one embodiment of the synthesis of 5-methylcytidine and thymidine derivatives of BCH-189 according to the present invention.
Figure 4:
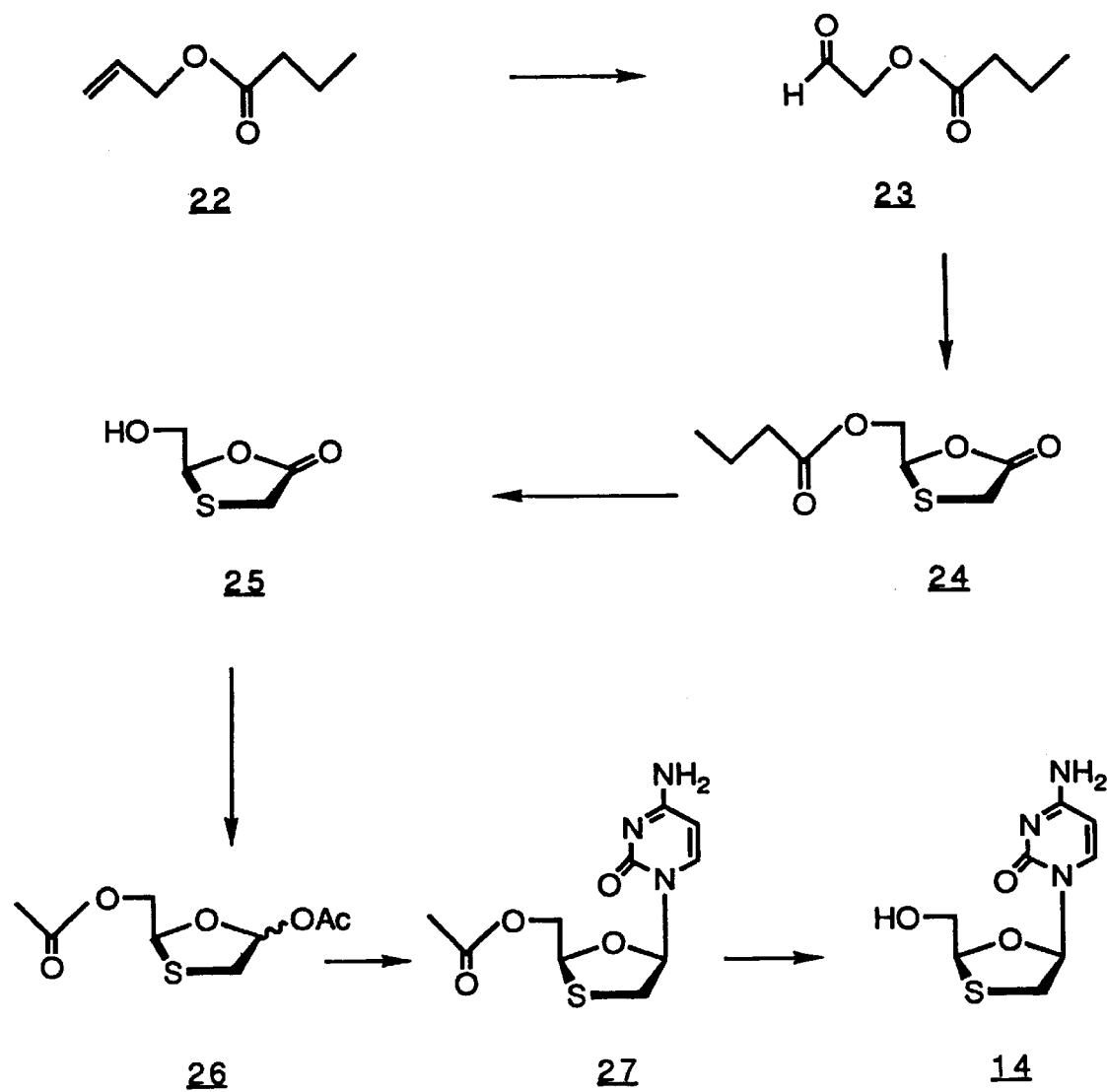
FIG. 4 illustrates one embodiment of the synthesis of enantiomerically-enriched BCH-189 according to the present invention.

Illustrative examples of the synthesis of BCH-189 or BCH-189 analogs according to the present invention are given in FIGS. 2, 3, and 4 and the following descriptions.

FIG. 2 shows the synthesis of BCH-189 starting with allyl alcohol 7. A NaH oil suspension (4.5 g, 60%, 110 mmol) was washed with THF twice (100 ml×2) and the resulting solid suspended in THF (300 ml). The suspension was cooled at 0° C., allyl alcohol 7 (6.8 ml, 100 mmol) was added dropwise, and the mixture was stirred for 30 minutes at 0° C. t-Butyl-diphenylsilyl chloride (25.8 ml, 100.8 mmol) was added dropwise at 0° C. and the reaction mixture was stirred for 1 hour at 0° C. The solution was quenched with water (100 ml), and extracted with diethyl ether (200 ml×2). The combined extracts were washed with water, dried over $MgSO_4$, filtered, concentrated, and the residue distilled under vacuum (90–100° C. at 0.5–0.6 mm Hg) to give a colorless liquid 8 (28 g., 94 mmol, 94%). ($^1$H NMR: 7.70–7.35 (10H, m, aromatic-H); 5.93 (1H, m, $H_2$); 5.37 (1H, dt, $H_1$) J=1.4 and 14.4 Hz; 5.07 (1H, dt, $H_1$) J-1.4 and 8.7 Hz; 4.21 (2H, m, $H_3$); 1.07 (9H, s, t-Bu)).

The silyl allyl ether 8 (15.5 g, 52.3 mmol) was dissolved in $CH_2Cl_2$ (400 ml), and ozonized at −78° C. Upon completion of ozonolysis, DMS (15 ml, 204 mmol, 3.9 eq) was added at −78° C. and the mixture was warmed to room temperature and stirred overnight. The solution was washed with water (100 ml×2), dried over $MgSO_4$, filtered, concentrated, and distilled under vacuum (100–110° C. at 0.5–0.6 mm Hg) to give a colorless liquid 9 (15.0 g, 50.3 mmol, 96%). ($^1$H NMR: 9.74 (1H, s, H—CO); 7.70–7.35 (10H, m, aromatic-H); 4.21 (2H, s, —$CH_2$); 1.22 (9H, s, t-Bu)).

Silayted glycoaldehyde 9 (15.0 g, 50.3 mmol) was dissolved in toluene (200 ml) and thioglycolic acid (3.50 ml, 50.3 mmol) was added all at once. The solution was refluxed for 2 hours while the resulting water was removed with a Dean-Stark trap. The solution was cooled to room temperature and washed with saturated $NaHCO_3$ solution and the aqueous washings were extracted with diethyl ether (200 ml×2). The combined extracts were washed with water (100 ml×2), dried over $MgSO_4$, filtered, and concentrated to give a colorless oil 10 (16.5 g, 44.3 mmol, 88%), which gradually solidified under vacuum. Recrystallization from hexane afforded a white solid 10 (15.8 g, 84%). ($^1$H NMR: 7.72–7.38 (10H, m, aromatic-H); 5.53 (1H, t, $H_2$) J=2.7 Hz; 3.93 (1H, dd, —$CH_2O$) J=9.3 Hz; 3.81 (1H, d, $1H_4$) J=13.8 Hz; 3.79 (1H, dd, —$CH_2O$); 3.58 (1H, d, $1H_4$); 1.02 (9H, s, t-Bu).

2-(t-Butyl-diphenylsilyloxy)-methyl-5-oxo-1,2-oxathiolane 10 (5.0 g, 13.42 mmol) was dissolved in toluene (150 ml) and the solution was cooled to −78° C. Dibal-H solution (14 ml, 1.0M in hexanes, 14 mmol) was added dropwise, while the inside temperature was kept below −70° C. all the time. After the completion of the addition, the mixture was stirred for 30 minutes at −78° C. Acetic anhydride (5 ml, 53 mmol) was added and the mixture was warmed to room temperature and stirred overnight. Water (5 ml) was added to the mixture and the resulting mixture was stirred for 1 hour at room temperature. The mixture was diluted with diethyl ether (300 ml), $MgSO_4$ (40 g) was added, and the mixture was stirred vigorously for 1 hour at room temperature. The mixture was filtered, concentrated, and the residue flash chromatographed with 20% ETOAc in hexanes to give a colorless liquid 11 (3.60 g, 8.64 mmol, 64%), which was a 6:1 mixture of anomers. ($^1$H NMR of the major isomer: 7.70–7.35 (10H, m, aromatic-H); 6.63 (1H, d, $H_5$) J=4.4 Hz; 5.47 (1H, t, $H_2$ 4.20–3.60 (2H, m, —$CH_2O$); 3.27 (1H, dd, $1H_4$) J-4.4 and 11.4 Hz; 3.09 (1H, d, $1H_4$) J=11.4 Hz; 2.02 (3H, s, $CH_3CO$); 1.05 (9H, s, t-Bu); $^1$H NMR of the minor isomer: 7.70–7.35 (10H, m, aromatic-H); 6.55 (1H, d, $H_5$) J=3.9 Hz; 5.45 (1H, t, $H_2$); 4.20–3.60 (2H, m, —$CH_2O$); 3.25 (1H, dd, $1H_4$) J=3.9 and 11.4 Hz; 3.11 (1H, d, $1H_4$) J=11.4 Hz; 2.04 (3H, s, $CH_3CO$); 1.04 (9H, s, t-Bu)).

2-(t-Butyl-diphenylsilyloxy)-methyl-5-acetoxy-1,3-oxathiolane 11 (0.28 g, 0.67 mmol) was dissolved in 1,2-dichloroethane (20 ml), and silyated cytosine 12 (0.20 g, 0.78 mmol) was added at once at room temperature. The mixture was stirred for 10 minutes and to it was added $SnCl_4$ solution (0.80 ml, 1.0 M solution in $CH_2Cl_2$, 0.80 mmol) dropwise at room temperature. Additional cytosine 12 (0.10 g, 0.39 mmol) and $SnCl_4$ solution (0.60 ml) were added in a same manner 1 hour later. After completion of the reaction in 2 hours, the solution was concentrated, and the residue was triturated with triethylamine (2 ml) and subjected to flash chromatography (first with neat EtOAc and then 20% ethanol in EtOAc) to give a tan solid 13 (100% β configuration) (0.25 g, 0.54 mmol, 80%). ($^1$H NMR (DMSO-$d^6$): 7.75 (1H, d, $H_6$) J=7.5 Hz; 7.65–7.35 (10H, m, aromatic-H); 7.21 and 7.14 (2H, broad, —$NH_2$); 6.19 (1H, t, $H_{5'}$); 5.57 (1H, d, $H_5$); 5.25 (1H, t, $H_{2'}$); 3.97 (1H, dd, —$CH_2O$) J=3.9 and 11.1 Hz; 3.87 (1H, dd, —$CH_2O$); 3.41 (1H, dd, $1H_{4'}$) J=4.5 and 11.7 Hz; 3.03 (1H, dd, $1H_{4'}$) J=?; 0.97 (9H, s, t-Bu)).

Silyether 13 (0.23 g, 0.49 mmol) was dissolved in THF (30 ml), and to it was added n-$Bu_4NF$ solution (0.50 ml, 1.0 M solution in THF, 0.50 mmol) dropwise at room temperature. The mixture was stirred for 1 hour and concentrated under vacuum. The residue was taken up with ethanol/triethylamine (2 ml/1 ml), and subjected to flash chromatography (first with EtOAc, then 20% ethanol in EtOAc) to afford a white solid 14 in 100% anomeric purity (BCH-189; 0.11 g, 0.48 mmol, 98%), which was further recrystallized from ethanol/$CHCl_3$/Hexanes mixture. ($^1$H NMR (DMSO-$d_6$): 7.91 (1H, d, $H_6$) J=7.6 Hz; 7.76 and 7.45 (2H, broad, —$NH_2$); 6.19 (1H, t, $H_{5'}$); 5.80 (1H, d, $H_5$) J=7.6 Hz; 5.34 (1H, broad, —OH); 5.17 (1H, t, $H_{2'}$); 3.74 (3.74 (2H, m, —$CH_2O$); 3.42 (1H, dd, $1H_{4'}$) J=5.6 and 11.5 Hz; 3.09 (1H, dd, $1H_{4'}$) J=4.5 and 11.5 Hz).

BCH-189 and its analogs can also be synthesized by coupling a silyated uracil derivative with 11. Silyated uracil derivative 15 (1.80 g, 7.02 mmol) was coupled with 11 (1.72 g, 4.13 mmol) in 1,2-dichloroethane (50 ml) in the presence of $SnCl_4$ (5.0 ml) as described above in the preparation of the cytosine derivative 13. The reaction was complete after 5 hours. Flash chromatography, first with 40% EtOAc in hexane and then EtOAc, afforded a white foam 16 (1.60 g, 3.43 mmol, 83%). ($^1$H NMR: 9.39 (1H, broad, —NH) 7.90 (1H, d, $H_6$) J=7.9 Hz; 7.75–7.35 (10H, m aromatic-H); 6.33 (1H, dd, $H_5$); 5.51 (1H, d, $H_5$) J=7.9 Hz; 5.23 (1H, t, $H_2$,); 4.11 (1H, dd, —$CH_2O$) J=3.2 and 11.7 Hz; 3.93 (1H, dd, —$CH_2O$); 3.48 (1H, dd, $1H_4$,) J=5.4 and 12.2 Hz; 3.13 (1H, dd, $1H_4$,) J=3.2 and 12.2 Hz).

The uracil derivative 16 can be converted to the cytosine derivative 13. The uracil derivative 16 (0.20 g, 0.43 mmol) was dissolved in a mixture of pyridine/dichloroethane (2 ml/10 ml), and the solution cooled to 0° C. Triflic anhydride (72 μl, 0.43 mmol) was added dropwise at 0° C. and the mixture was warmed to room temperature and stirred for 1 hour. Additional triflic anhydride (0.50 μl, 0.30 mmol) was added and the mixture stirred for 1 hour. TLC showed no mobility with EtOAc. The reaction mixture was then decannulated into a $NH_3$-saturated methanol solution (30 ml) and the mixture was stirred for 12 hours at room temperature. The solution was concentrated, and the residue subjected to flash chromatography to give a tanned foam 13 (0.18 g, 0.39 mmol, 91%), which was identical with the compound obtained from the cytosine coupling reaction.

FIG. 3 illustrates the synthesis of 5-methylcytidine and thymidine derivatives of BCH-189. The acetate 11 (0.93 g, 2.23 mmol) in 1,2-dichloroethane (50 ml), was reacted with the silylated thymine derivative 17 (1.0 g, 3.70 mmol), and $SnCl_4$ solution (4.0 ml) in a manner similar to that described for the preparation of cytosine derivative 13. ($^1$H NMR: 8.10 (1H, broad, NH); 7.75–7.30 (11H, m, 10 Aromatic H's and $1H_6$); 6.32 (1H, t, $H_1$,) J=5.4 Hz; 5.25 (1H, t, $H_4$,) J=4.2 Hz; 4.01 (1H, dd, $1H_5$,) J=3.9 and 11.4 Hz; 3.93 (1H, dd, $1H_5$,) J=4.5 and 11.4 Hz; 3.41 (1H, dd, $1H_2$,) J=5.4 and 11.7 Hz; 3.04 (1H, dd, $1H_2$,) J=5.7 and 11.7 Hz; 1.75 (3H, s, $CH_3$); 1.07 (9H, s, t-Bu)).

The thymine derivative 18 (0.20 g, 0.42 mmol) was dissolved in a mixture of pyridine/dichloroethane (2 ml/10 ml), and the solution cooled to 0° C. To it was added triflic anhydride (100 μl, 0.60 mmol) dropwise at 0° C., and mixture was allowed, with continuous stirring, to warm to room temperature. After reaching room temperature, it was stirred for 1 hour. TLC showed no mobility with EtOAc. The reaction mixture was then decannulated into the NH 3-saturated methanol solution (20 ml), and the mixture stirred for 12 hours at room temperature. The solution was concentrated, and the residue was subjected to flash chromatography to give a tanned foam 19 (0.18 g, 0.38 mmol, 90%). ($^1$H NMR: 7.70–7.30 (12H, m, 10 Aromatic H's, 1NH and $H_6$); 6.60 (1H, broad, 1NH); 6.34 (1H, t, $H_1$,) J=4.5 Hz; 5.25 (1H, t, $H_4$,) J=3.6 Hz; 4.08 (1H, dd, $1H_5$,) J=3.6 and 11.4 Hz; 3.96 (1H dd, $1H_5$,) J=3.6 and 11.4 Hz; 3.52 (1H, dd, $1H_2$,) J=5.4 and 12.3 Hz; 3.09 (1H, dd, $1H_2$,) J=3,9 and 12.3 Hz; 1.72 (3H, s, $CH_3$); 1.07 (9H, s, t-Bu)).

Silylether 19 (0.18 g, 0.38 mmol) was dissolved in THF (20 ml), and an n-$Bu_4NF$ solution (0.50 ml, 1.0 M solution in THF, 0.50 mmol) was added, dropwise, at room temperature. The mixture was stirred for 1 hour and concentrated under vacuum. The residue was taken up with ethanol/triethylamine (2 ml/1 ml), and subjected to flash chromatography (first with EtOAc, then 20% ethanol in EtOAc) to afford a white solid 20 (0.09 g, 0.37 mmol, 97%), which was further recrystallized from ethanol/$CHCl_3$/Hexanes mixture to afford 82 mg of pure compound (89%). ($^1$H NMR: (in $d^6$-DMSO): 7.70 (1H, s, $H_6$); 7.48 and 7.10 (2H, broad, $NH_2$); 6.19 (1H, t, $H_1$,) J=6.5 Hz; 5.31 (1H, t, OH);5.16 (1H, t, $1H_4$,) J=5.4 Hz; 3.72 (2H, m, $2H_5$,) 3.36 (1H, dd, $1H_2$,) J=6.5 and 14.0 Hz; 3.05 (1H, dd, $1H_2$,) J=6.5 and 14.0 Hz; 1.85 (3H, s, $CH_3$)).

Silylether 18 (0.70 g, 1.46 mmol) was dissolved in THF (50 ml), and an n-$Bu_4NF$ solution (2 ml, 1.0 M solution in THF, 2 mmol) was added, dropwise, at room temperature. The mixture was stirred for 1 hour and concentrated under vacuum. The residue was taken up with ethanol/triethylamine (2 ml/1 ml), and subjected to flash chromatography to afford a white solid 21 (0.33 g, 1.35 mmol, 92%). ($^1$H NMR: (in $d^6$-Acetone): 9.98 (1H, broad, NH); 7.76 (1H, d, $H_6$) J=1.2 Hz; 6.25 (1H, t, $H_4$,) J=5.7 Hz; 5.24 (1H, t, $H_1$,) J=4.2 Hz; 4.39 (1H, t, OH) J=5.7 Hz; 3.85 (1H, dd, $2H_5$,) J=4.2 and 5.7 Hz; 3.41 (1H, dd, $1H_2$,) J=5.7 and 12.0 Hz; 3.19 (1H, dd, $1H_2$,) J=5.4 and 12.0 Hz; 1.80 (3H, S, $CH_3$)).

FIG. 4 illustrates the synthesis of enantiomerically-enriched BCH-189 and its analogs. Allyl butyrate 22 (19.0 g, 148 mmol) was dissolved in $CH_2Cl_2$ (400 ml), and ozonized at –78° C. Upon completion of ozonolysis, dimethyl sulfide (20 ml, 270 mmol, 1.8 eq) was added at –78° C. and the mixture was warmed to room temperature and stirred overnight. The solution was washed with water (100 ml×2), dried over $MgSO_4$, filtered, concentrated, and distilled under vacuum (70–80° C. at 0.5–0.6 mm Hg) to give a colorless liquid 23 (17.0 g, 131 mmol, 88%). ($^1$H NMR: 9.59 (1H, s, H—CO); 4.66 (2H, s, —$CH_2O$); 2.42 (2H, t, $CH_2CO$) J=7.2 Hz; 1.71 (2H, sex, —$CH_2$); 0.97 (3H, t, $CH_3$) J=7.2 Hz) (IR neat): 2990, 2960, 2900, 1750, 1740, 1460, 1420, 1390, 1280, 1190, 1110, 1060, 1020, 990, 880, 800, 760).

Butyryloxyacetaldehyde 23 (15.0 g, 115 mmol) was dissolved in toluene (200 ml) and mixed with thioglycolic acid (8.0 ml, 115 mmol). The solution was refluxed for 5 hours while the resulting water was removed with a Dean-Stark trap. The solution was cooled to room temperature and was transferred to a 500 ml separatory funnel. The solution was then washed with saturated $NaHCO_3$ solution. These aqueous washing were extracted with diethyl ether (200 ml×2) to recuperate any crude product from the aqueous layer. The ether extracts were added to the toluene layer and the resulting mixture was washed with water (100 ml×2), dried over $MgSO_4$, filtered concentrated, and distilled under vacuum (70–80°C. at 0.5–0.6 mm Hg) to give a colorless oil 24 (19 g, 93 mmol, 81%). ($^1$H NMR: 5.65 (1H, dd, $H_5$) J=5.0 and 1.4 Hz; 4.35 (1H, dd, —$CH_2O$) J=3.2 and 12.2 Hz; 4.29 (1H, dd, —$CH_2O$) J=5.7 and 12.2 Hz; 3.72 (1H, d, —$CH_2S$) J=16.2 Hz; 3.64 (1H, d, —$CH_2S$; 2.34 (2H, t, —$CH_2CO$) J=7.2 Hz; 1.66 (2H, sex, —$CH_2$); 0.95 (3H, t, $CH_3$) J=7.2 Hz) (IR (neat): 2980, 2960, 2900, 1780, 1740, 1460, 1410, 1390, 1350, 1300, 1290, 1260, 1220, 1170, 1110, 1080, 1070, 1000, 950, 910, 830, 820, 800, 760).

Pig liver esterase solution (90 μl) was added to a buffer solution (pH 7, 100 ml) at room temperature, and the mixture stirred vigorously for 5 minutes. The butyrate 24 (2.8 g, 13.7 mmol) was added, all at once, to the esterase/buffer solution and the mixture was stirred vigorously at room temperature for 2 hours. The reaction mixture was poured into a separatory funnel. The reaction flask was washed with ether (10 ml) and the washing was combined with the reaction mixture in the funnel. The combined mixture was extracted with hexanes three times (100 ml×3). The three hexane extracts were combined and dried over MgSO4, filtered, and concentrated to give the optically active butyrate 24 (1.12 g, 5.48 mmol, 40%). Enantiomeric excess was determined by an NMR experiment using a Tris[3-heptafluoropropyl-hydroxymethylene)-(+)-camphorato] europium (III) derivative as a chemical shift reagent; this procedure showed approximately 40% enrichment for one enantiomer. The remaining aqueous layer from the reaction was subjected to a continuous extraction with $CH_2Cl_2$ for 20 hours. The organic layer was removed from the extraction apparatus, dried over $MgSO_4$, filtered, and concentrated to give an oil (1.24 g), which was shown by NMR analysis to consist of predominately the 2-hydroxymethyl-5-oxo-1,3-oxathiolane 25 with small amounts of butyric acid and the butyrate 24.

The lactone 25 (0.85 g, 4.16 mmol) was dissolved in toluene (30 ml), and the solution cooled to −78° C. Dibal-H solution (9 ml, 1.0 M in hexanes, 9 mmol) was added dropwise, while the inside temperature was kept below −70° C. throughout the addition. After the addition was completed, the mixture was stirred for 0.5 hours at −78° C. Acetic anhydride (5 ml, 53 mmol) was added and the mixture, with continuous stirring, was allowed to reach room temperature overnight. Water (5 ml) was added to the reaction mixture and the resultant mixture was stirred for 1 hour. $MgSO_4$ (40 g) was then added and the mixture was stirred vigorously for 1 hour at room temperature. The mixture was filtered, concentrated, and the residue flash chromatographed with 20% EtOAc in hexanes to give a colorless liquid 26 (0.41 g, 1.86 mmol, 45%) which was a mixture of anomers at the C-4 position.

The 2-Acetoxymethyl-5-acetoxy-1,3-oxathiolane 26 (0.40 g, 1.82 mmol) was dissolved in 1,2-dichloroethane (40 ml), and to it the silylated cytosine 12 (0.70 g, 2.74 mmol) was added, all at once, at room temperature. The mixture was stirred for 10 minutes, and to it a $SnCl_4$ solution (3.0 ml, 1.0 M solution in $CH_2Cl_2$, 3.0 mmol) was added, dropwise, at room temperature. Additional $SnCl_4$ solution (1.0 ml) was added after 1 hour. The reaction was followed by TLC. Upon completion of the coupling, the solution was concentrated, the residue was triturated with triethylamine (2 ml) and subjected to flash chromatography (first with neat EtOAc then 20% ethanol in EtOAc) to give a tan solid 27 (0.42 g, 1.55 mmol, 86%). ($^1$H NMR: 7.73 (1H, d, $H_6$) J=7.5 Hz; 6.33 (1H, t, $H_{4'}$) J=4.8 Hz; 5.80 (1H, d, $H_5$) J=7.5 Hz; 4.52 (1H, dd, $1H_{5'}$) J=5.7 and 12.3 Hz; 4.37 (1H, dd, $1H_{5'}$) J=3.3 and 12.3 Hz; 3.54 (1H, dd, $H_{2'}$,) J=5.4 and 12.0 Hz; 3.10 (1H, dd, $1H_3$); 2.11 (3H, s, $CH_3$).

The 5'-Acetate of BCH-189 27 (140 mg. 0.52 mmol) was dissolved in anhydrous methanol (10 ml), and to it was added sodium methoxide (110 mg, 2.0 mmol) in one portion. The mixture was stirred at room temperature until the hydrolysis was complete. The hydrolysis took about 1 hour, and the reaction was followed by TLC. Upon completion, the mixture was then concentrated, and the residue taken up with ethanol (2 ml). The ethanol solution was subjected to column chromatography using ethyl acetate first, then 20% ethanol in EtOAc to afford a white foam (110 mg, 92%), which exhibited an NMR spectrum identical to that of authentic BCH-189, 14.

What is claimed is:

1. A method of preparing the B-isomer of a 1,3-oxathiolane nucleoside, comprising reacting a compound of the structure:

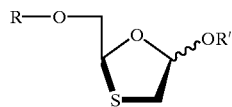

wherein R' is an acyl group and R is an oxygen protecting group, with a protected pyrimidine base in the presence of $SnCl_4$.

* * * * *